(12) United States Patent
Studer

(10) Patent No.: US 9,623,581 B2
(45) Date of Patent: Apr. 18, 2017

(54) DEVICE FOR TRANSFERRING SECTION RIBBON TO SPECIMEN HOLDER FOR TRANSMISSION ELECTRON MICROSCOPY, AND METHOD FOR ITS USE

(71) Applicant: Daniel Studer, Dotzigen (CH)

(72) Inventor: Daniel Studer, Dotzigen (CH)

(*) Notice: Subject to any disclaimer, the term of this patent is extended or adjusted under 35 U.S.C. 154(b) by 316 days.

(21) Appl. No.: 14/285,267

(22) Filed: May 22, 2014

(65) Prior Publication Data
US 2014/0345433 A1    Nov. 27, 2014

(30) Foreign Application Priority Data
May 22, 2013  (EP) .................................... 13405063

(51) Int. Cl.
*B26D 7/01*   (2006.01)
*G01N 1/06*   (2006.01)
*G01N 1/28*   (2006.01)
*G01N 1/42*   (2006.01)

(52) U.S. Cl.
CPC ............... *B26D 7/01* (2013.01); *G01N 1/06* (2013.01); *G01N 1/2813* (2013.01); *G01N 1/42* (2013.01); *H01J 2237/20* (2013.01); *Y10T 83/6572* (2015.04)

(58) Field of Classification Search
CPC .......... B26D 7/01; B26D 1/1575; B26D 1/00; G01N 1/2813; G01N 1/06; G01N 1/42; H01J 2237/20; B20D 1/105; Y10T 83/6571; Y10T 83/6508; Y10T 83/6572; Y10T 83/283; Y10T 83/222

USPC ......... 83/418, 167, 170, 713, 417, 168, 414, 83/701, 915.5, 169
See application file for complete search history.

(56) References Cited

U.S. PATENT DOCUMENTS

| | | | | |
|---|---|---|---|---|
| 3,733,948 A | * | 5/1973 | Pickett ................... | G01N 1/06 134/191 |
| 5,713,255 A | * | 2/1998 | Izvozichikov ........... | G01N 1/06 83/106 |
| 7,600,457 B2 | * | 10/2009 | Voneiff .................... | G01N 1/06 83/307.1 |
| 8,109,184 B2 | * | 2/2012 | Kong ....................... | G01N 1/06 83/13 |

(Continued)

OTHER PUBLICATIONS

Ladinsky, Mark A. et al, Chapter Eight: Micromanipulator-Assisted Vitreous Cryosectioning and Sample Preparation by High-Pressure Freezing, Methods in Enzymology, 2010, pp. 165-194, vol. 481, Elsevier, Inc., Pasadena, California, USA.

(Continued)

*Primary Examiner* — Ghassem Alie
(74) *Attorney, Agent, or Firm* — Mark A. Oathout; Oathout Law Firm

(57) ABSTRACT

A device has two mutually independent tools first to manipulate the section ribbons and second to manipulate the specimen holders (grids). Each of the tools can be positioned independently during the cutting process by two mutually independent micromanipulators. The tool for manipulating the section ribbons has a metal tube, a tube of an electrically insulating material and an exchangeable tip. A resilient fiber of dielectric material fitted with an electrically conductive surface coating is exchangeably mounted in the tip and is used for delicate handling of the section ribbons.

19 Claims, 18 Drawing Sheets

(56) References Cited

U.S. PATENT DOCUMENTS

2009/0183613 A1    7/2009  Lihl et al.

OTHER PUBLICATIONS

Ladinsky, Mark A. et al., Vitreous Cryo-Sectioning of Cells Facilitated by a Micromanipulator, The Authors, Journal of Microscopy, 2006, pp. 129-134, vol. 224, University of Colorado, Boulder, CO, USA.

Pierson, Jason et al., Improving the technique of vitreous cryo-sectioning for cryo-electron tomography: Electrostatic charging for section attachment and implementation of an anti-contamination glove box, Journal of Structural Biology, 2009, pp. 219-225, Elsevier, Inc., USA.

Bockstahl, Frederic, European Search Report, Jan. 6, 2014, 1 page, European Patent Office, Europe.

\* cited by examiner

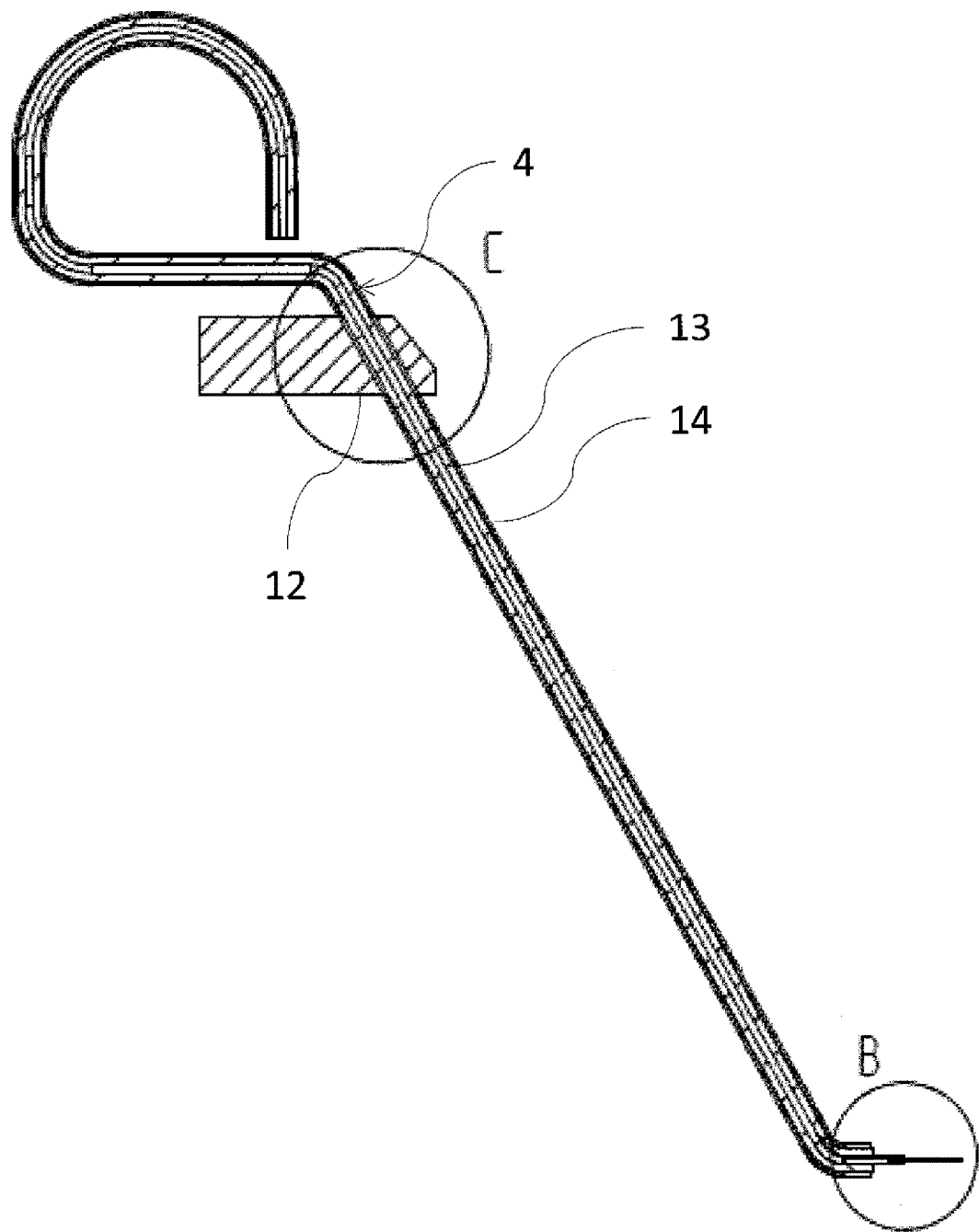

Detail C

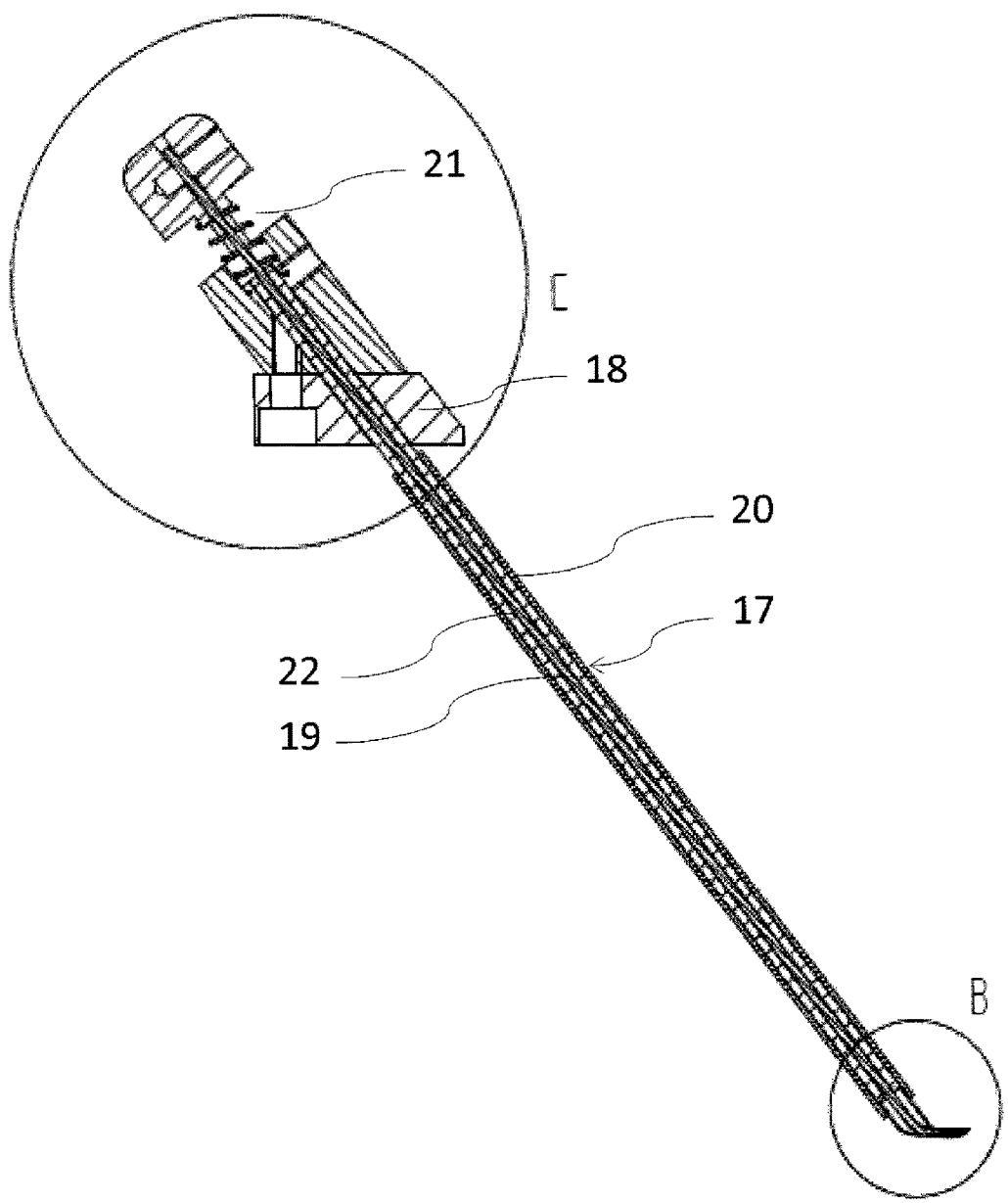

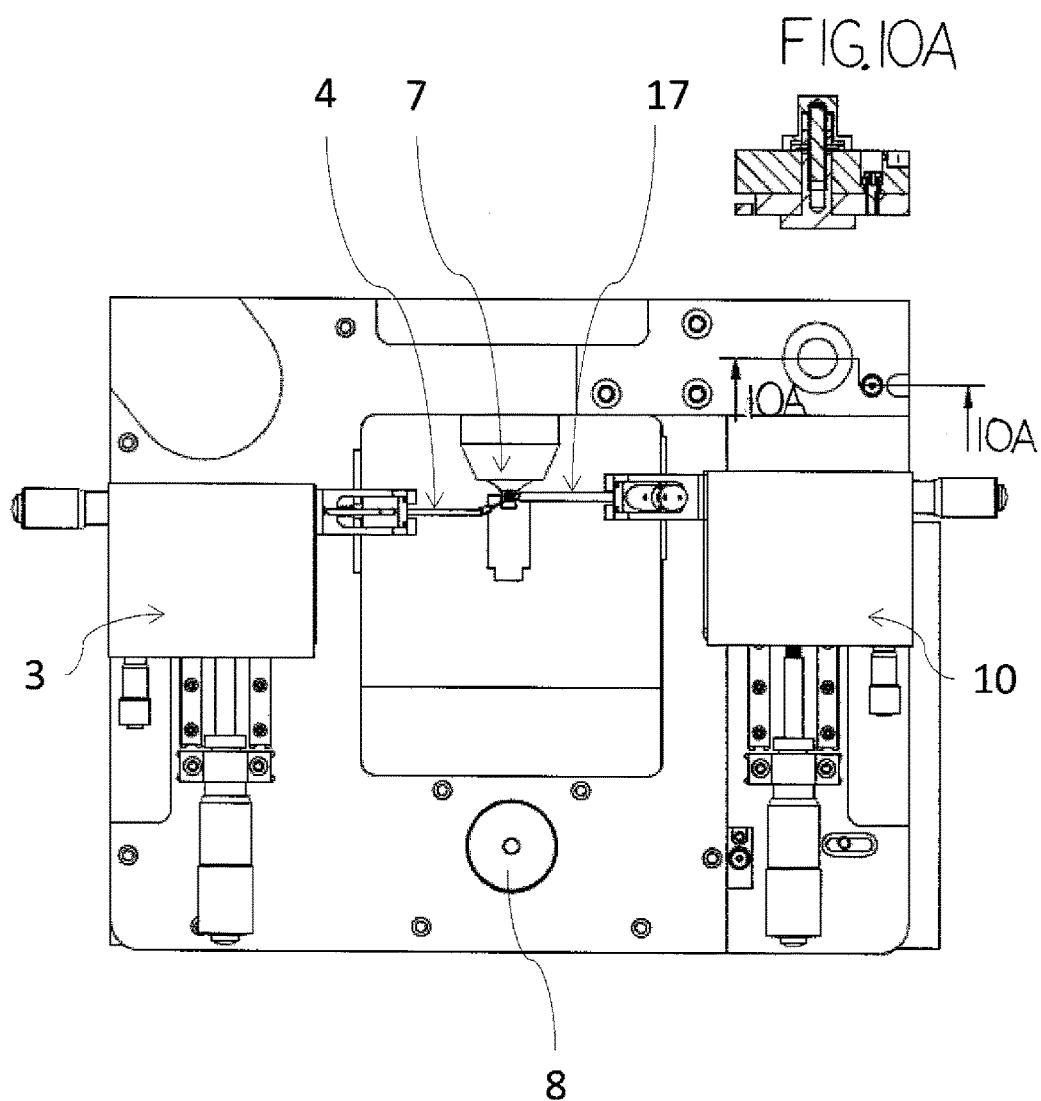

DEVICE FOR TRANSFERRING SECTION RIBBON TO SPECIMEN HOLDER FOR TRANSMISSION ELECTRON MICROSCOPY, AND METHOD FOR ITS USE

The production of ultrathin cryosections (dry cutting) of usually, but not exclusively, biological specimens has proved a critical phase in the examination of objects in transmission electron microscopy (TEM), which determines the success of the process. In TEM, only very thin solid bodies can be examined. A reasonable thickness of a biological specimen is less than 200 nm. In order to convert a biological specimen into a solid body, in the traditional process the specimen is fixed, normally by aldehyde, the water is replaced with solvent and the specimen is embedded in a polymer by substitution of the solvent, and then cut ultrathin on water. With this method, the specimen loses all water, i.e. 60% to 80% of the mass of a biological specimen is lost and artefacts are necessarily induced. The alternative is to vitrify the specimens, i.e. freeze the specimens rapidly so that the water in the biological structures does not form ice crystals during cooling, and from this produce cryosections which are examined on a TEM cryoholder at around 100° K. (Al-Amoudi et al., EMBO J. 2004, 23(18):3583-8).

According to this process, ultrathin cryosections are produced as follows: The specimen must be vitrified, i.e. be extremely viscous or quasi-solid at 100° K., and free from ice crystals, because specimens which contain ice crystals are brittle and almost impossible to cut. For preparation, the specimen is frozen in or on a specimen holder or reliably fixed by other means. The specimen which is prepared in this way is fixed in a pre-cooled cryo-ultramicrotome (usually at 110° K.) for cryosectioning. The microtome arm is introduced into the cryostat where it collects the vitrified specimen and controls the advance and cutting movement.

The specimen is then trimmed with a special trimming diamond knife. The result of trimming is normally a truncated pyramid which consists of the biological material of interest. The top square of the truncated pyramid has a side length of around 150 μm and protrudes by approximately 30 μm.

After trimming, the specimen is normally cut ultrathin at 110° K. using a diamond knife with a nominal advance of around 50 nm (layer thickness 50-70 nm), with a cutting speed of for example 1 mm s$^{-1}$. This cryosectioning causes a compression of the sections of up to 50% in the cut direction, i.e. the volume of the section remains constant, the edge length of the cut square lying in the cutting direction is reduced by half, and the section thickness is twice as thick. By ionizing the cutting environment (distance from knife edge around 15-20 mm) with a commercially available ionizer (for example CRION for Leica EM FC 7 from Leica-Microsystems or Static-Line Ionizer from Diatome US), the compression can be reduced but is not totally prevented.

The vitrified specimens form section ribbons on the diamond knife edge, i.e. the first section adheres to the second section and is pushed down by this on the knife surface. When the short section ribbon succeeds in adsorbing the first sections (which is not normally achievable permanently) by mounting on a fiber tip, for example a human eyelash, or an animal hair (for example a Dalmatian dog fur hair or guinea pig fur hair), a longer section ribbon with a plurality of individual sections can be produced if the section ribbon is guided away from the cut edge by this fiber. Alternatively, the fiber can catch on an often self-forming loop of the short section ribbon. This too does not give a permanent connection between the fiber and the section ribbon. Both these approaches are very demanding, difficult steps in the production of cryosections since the fiber is guided manually, which requires great concentration with fine motor control and can usually be performed successfully only by a few operators.

Alternatively, the fiber can be attached to the end of a suitably dimensioned moulding (e.g. rod) of heat-insulating material, which in turn can be clamped in the arm of a commercial micromanipulator (for example Micromanipulator-M by Leica Microsystems GmbH). This allows the fiber to be moved with precision control in the microregion using the manipulator (M. S. Ladinsky et al., Journal of Microscopy 224 (2006), 130). Fixing the first section to the fiber remains difficult. A permanent connection between the fiber and the section ribbon is not possible.

The section ribbon which is prepared in this way is then attached to a specimen holder which is suitable for TEM, usually with a grid with a mesh width of 50-100 μm. This step is usually carried out manually: the operator guides the grid, for example a 200-mesh molybdenum-based grid coated with a carbon film (for example EM Sciences, Hatfield, USA) below the section ribbon, which is still connected to the diamond knife edge, and makes contact with this by moving the grid vertically from bottom to top.

Alternatively, after reaching the desired length, the section ribbon which is guided by a micromanipulator with the fiber can be brought into contact with the grid by lowering in the vertical direction with the micromanipulator. A second fiber is then used to slide the section ribbon onto the grid, or press this as required, and finally it is separated from the rest of the section ribbon as closely as possible to the diamond knife (Ladinsky et al., ibid., page 130 and 132, FIG. 2B).

According to Ladinsky et al., the adhesion of the section ribbon to the grid is achieved by mechanical pressing. This method is not very efficient; often sections are lost. Pierson et al. (2010, J Struct Biol. 1692: 220-221, in particular FIG. 1 page 221) therefore attach the sections to the grid using an ionizer (DE publication 10 2008 059 284 of Jul. 30, 2009 and CRION for Leica EM FC 7, both from Leica-Microsystems GmbH, or Static-Line Ionizer by Diatome US). In normal ionization (discharge mode), the electrode which is installed close to the knife edge causes a reduction in the electrostatic effect (which for example is responsible for the often strong adsorption of the sections which are formed on the knife edge to the surface of the knife) and thus improves the sliding of the sections during or after the cutting process (Leica EM FC7 product information, Leica Microsystems GmbH 2013, page 7).

Pierson et al. found that section ribbons could be applied firmly to an electrically conductive, carbon-coated grid by ionization. For this, normal ionization (discharge mode) was switched off and an earthed grid was brought from below into contact with the section ribbon. At the time of contact of the section ribbon and grid, using the same ionizer in charge mode, a brief (less than 1 sec.) increased ionization pulse was triggered, causing the section ribbon to adhere irreversibly to the grid. In practice therefore, simply by switching on the ionizer (charge mode), preferably by means of a foot pedal, the operator can start the ionization on the surface of the section ribbon and hence attach the section ribbon to the grid (Pierson et al. 2010, J Struct Biol. 1692: 220-221, in particular FIG. 1 page 221, Leica EM FC 7 product information, pages 11/12).

The object of the present invention is to simplify and improve the handling of ultrathin section ribbons which are produced in ultramicrotomes.

Also using a micromanipulator, the application of the first section of a section ribbon to the fiber (hair) introduced by Ladinsky et al. is usually only possible with additional manual support. In comparison with this difficult manual preparation on the fiber, the object of the invention is therefore to reduce the manual requirements for the performing operator and thus ensure that even averagely-trained and skilled technical personnel are able to prepare perfect specimens of section ribbons in great quantities.

In relation to micromanipulation with a non-electrically-conductive fiber of a dielectric such as animal or human hair (eyelash) or a non-conductive plastic (nylon etc.), the object of the invention is to increase the speed and reproducibility of the preparation of section ribbons and integrate all necessary instruments into one easy-to-operate device.

This object is achieved by a device according to the features of claim 1 and by a method for its use according to the features of claim 21.

The device according to the invention substantially increases the reproducibility of the results of the preparation and practically completely eliminates the rejection level. The work sequences for preparation using the device according to the invention are simplified such that the preparation can be carried out reliably by averagely-trained technical personnel with average manual dexterity.

The method of handling section ribbons is greatly simplified with the section ribbon manipulator according to the invention and the grid holder which is also easy to manipulate. This manipulator precisely guides a tip, which is mounted to be easily exchanged on the end of the manipulator. This tip (fiber) for example consists of an animal or human hair (eyelash, bristle) or a fiber of a suitable dielectric material (for example plastic or glass). The surface of this fiber is made electrically conductive by coating (for example by vapour deposition in high vacuum or by treatment with a sputter source) with a suitable, electrically conductive, surface layer (preferably gold, another metal or carbon) and can thus be earthed. The fiber should be as soft as possible so that any contact with the delicate cutting edge during manipulation does not damage it. The use of a fine metal wire which increases in hardness and stiffness in the cold is therefore of only limited suitability.

The electrically conductive tip of the fiber is positioned behind the section ribbon which is forming on the knife of the microtome. Then using a commercially available ionizer (see above, CRION for Leica EM FC 7 by Leica Microsystems or Static-Line Ionizer by Diatome US), the section ribbon is attached to the earthed tip by increasing the ionization. The distance between the tip of the ionizer and the tip (fiber) of the section ribbon manipulator is preferably around 1.5 cm.

In comparison with a non-electrically-conductive fiber which is guided by the micromanipulator, the device according to the invention with the electrically conductive surface of the fiber has the advantage that the end of the section ribbon can be affixed to the earthed tip by the ionizer easily and substantially more quickly and more precisely, and gives a permanent attachment of the section ribbon to the tip of the fiber. The permanent connection between the conductive fiber and the section ribbon can only be undone by destruction, i.e. tearing off the sections which are not connected to the fiber from the sections which are attached to the fiber. With a fiber of dielectric material, no comparable permanent connection is possible.

This fixed connection between the conductive fiber and the section ribbon is of great benefit. For example, the isolation intensity in discharge mode, which can cause the section ribbon to oscillate, is not as critical as when the section ribbon is attached loosely with a non-conductive fiber. Also, with a permanent connection between the conductive fiber and section ribbon, it is possible to counter sudden section deformations which can for example be attributed to a not totally homogenous specimen, in that for example the tension of the fiber on the section ribbon can vary or its direction can change slightly. If the fiber is firmly connected with the short section ribbon, an unsuccessful guidance of the section ribbon which is formed by the sections produced by the microtome is almost excluded, since the micromanipulator with which the fiber tip is guided easily executes the necessary movements. If the fiber is not electrically conductive and cannot therefore be permanently connected with the section ribbon, the section ribbon can be detached from this non-conductive tip, which makes manipulation correspondingly more difficult and time-consuming.

When the resulting short section ribbon is firmly connected to the fiber tip by way of the electrostatic attraction, it is guided on the earthed tip of the section ribbon manipulator using a conventional micromanipulator so as to give a cohesive section ribbon as long as possible. The section ribbon usually has a length of slightly more than 3 mm and thus extends over the entire diameter of a conventional TEM grid.

A second micromanipulator is arranged on the opposite edge of the device, which can be rotated away around a vertical axis and carries a grid holder (see DE publication 10 2008 059 284 dated Jul. 30, 2009, FIGS. 3 and 4). The TEM grid which is fixed to this grid holder is first moved into the desired position vertically below the section ribbon, then brought upwardly from below into contact with this section ribbon, and then the section ribbon is connected to the grid by an ionization stroke in the "charge" mode. The grid holder allows the grid with the attached sections to be transferred very quickly into a commercial storage container (Gatan) which for example is prepared in liquid nitrogen.

The adhesion and guidance of the section ribbon with a non-conductive dielectric fiber (hair), which is difficult both manually and with the use of a micromanipulator, and the transfer of the section ribbon using the fiber onto the grid, which is carried out manually or with a micromanipulator, are substantially simplified by the device according to the invention. The advantage lies above all in the simplified and improved fixing of the cryosection ribbons to an electrically conductive tip, i.e. the creation of a permanent connection between the tip and the section ribbon. For selection and training of the operators, this gives the advantage that no highly developed fine motor control is required to produce cryosections successfully, since all demanding steps are carried out by micromanipulators which are easy to operate. Also, the fixing and exchange of the grid of a material suitable for TEM are simple and efficient. Since the grid can also be changed and manipulated simply and easily, a further advantage of the device according to the invention results.

When the section ribbon is applied to the TEM grid, it is transferred into liquid nitrogen as quickly as possible in order to minimise contamination with ice crystals. The result is a substantially lower contamination with ice crystals than with the conventional manual method. This is decisive for the success of the method since electrons cannot propagate through small ice crystals (diameter<0.5 microns). The grid holder transfers the grid with the section ribbon into a commercial storage container in a very simple manner.

As a result, the method according to the invention massively increases the chances of success and the operating reliability of the production of section ribbons, in particular of cryosection ribbons, and thus also increases the chances of success of examination of the section ribbons produced in this way by means of TEM.

The section ribbon manipulator according to the invention also allows easier handling after cutting of dry-cut specimens which are embedded in polymer, wherein the method in this case is carried out at room temperature without cooling.

BRIEF DESCRIPTION OF THE DRAWINGS

Preferred embodiments of the device according to the invention and their use are explained below with reference to drawings which are given as examples, wherein the invention is not restricted to the particular embodiments shown. In the drawings:

FIG. 3B shows a longitudinal section through the section ribbon manipulator according to line 3B-3B of FIG. 3A, FIG. 4B shows a longitudinal section through the grid holder according to line 4B-4B of FIG. 4A.

FIG. 5A phase I of the section manipulation in the cryostat: starting position, in top view, FIG. 5B phase II of the section manipulation in the cryostat: attaching the section ribbon to the fiber tip, in top view, FIG. 5C phase II in side view, FIG. 6A phase III of the section manipulation in the cryostat: extraction of the section ribbon, in top view, FIG. 6B phase III in side view, FIG. 7A phase IV of the section manipulation in the cryostat: positioning of the grid below the section ribbon, FIG. 7B phase IV in side view, FIG. 8A phase V, grid with section ribbon applied, after removal of the section ribbon manipulator with the fiber tip, in top view, FIG. 8B phase V in side view, FIG. 9A phase VI grid with section ribbon applied, after removal from the microtome, FIG. 9B phase VI in side view, FIG. 10 overall view of the device in top view during phase V.

FIG. 10A shows a section view according to line 10A-10A of FIG. 10.

DETAILED DESCRIPTION

Figure 1A:
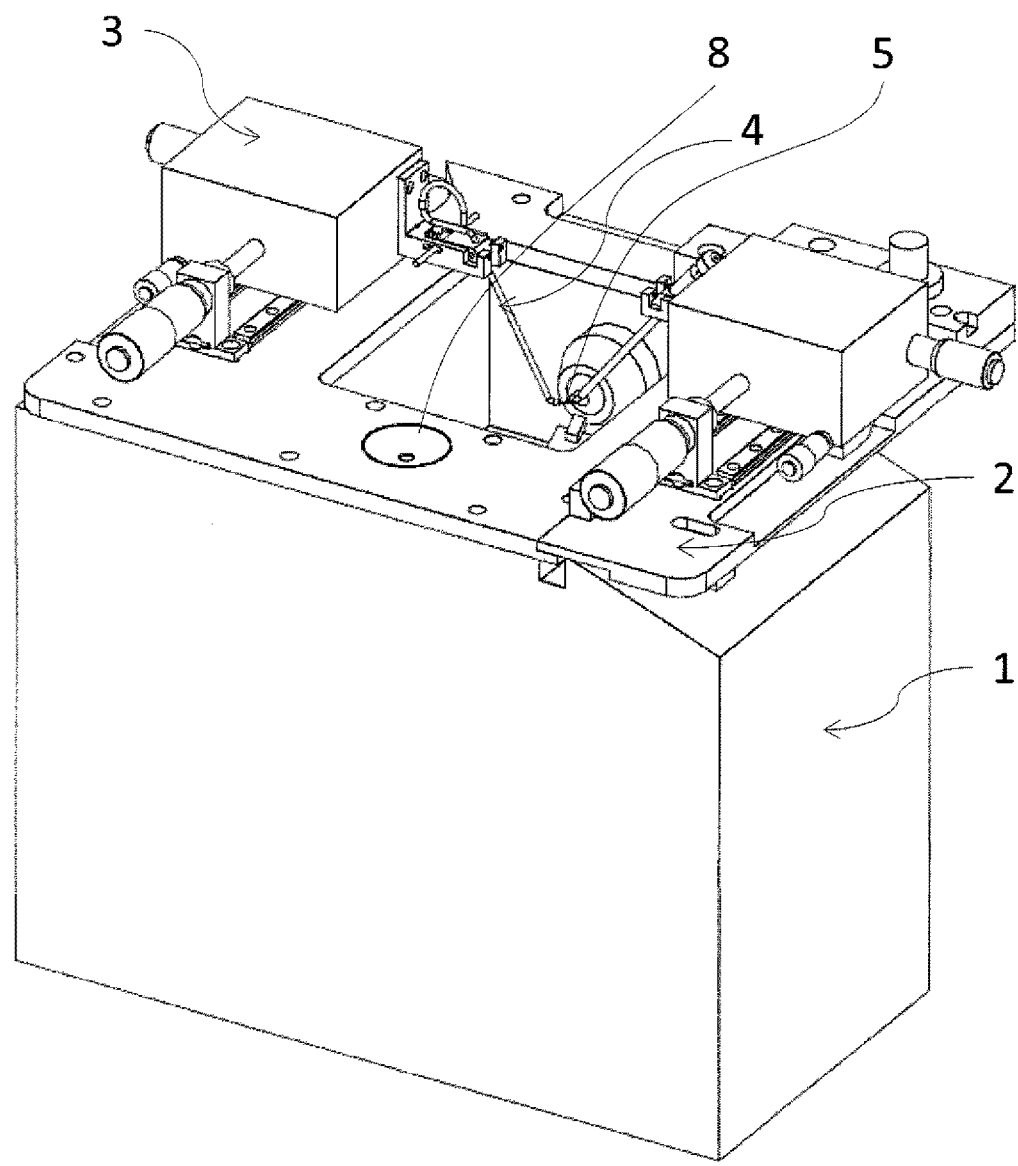
FIG. 1A shows an overall view of the device constructed on a schematically sketched, commercial cryostat without ionization device.
Figure 2:
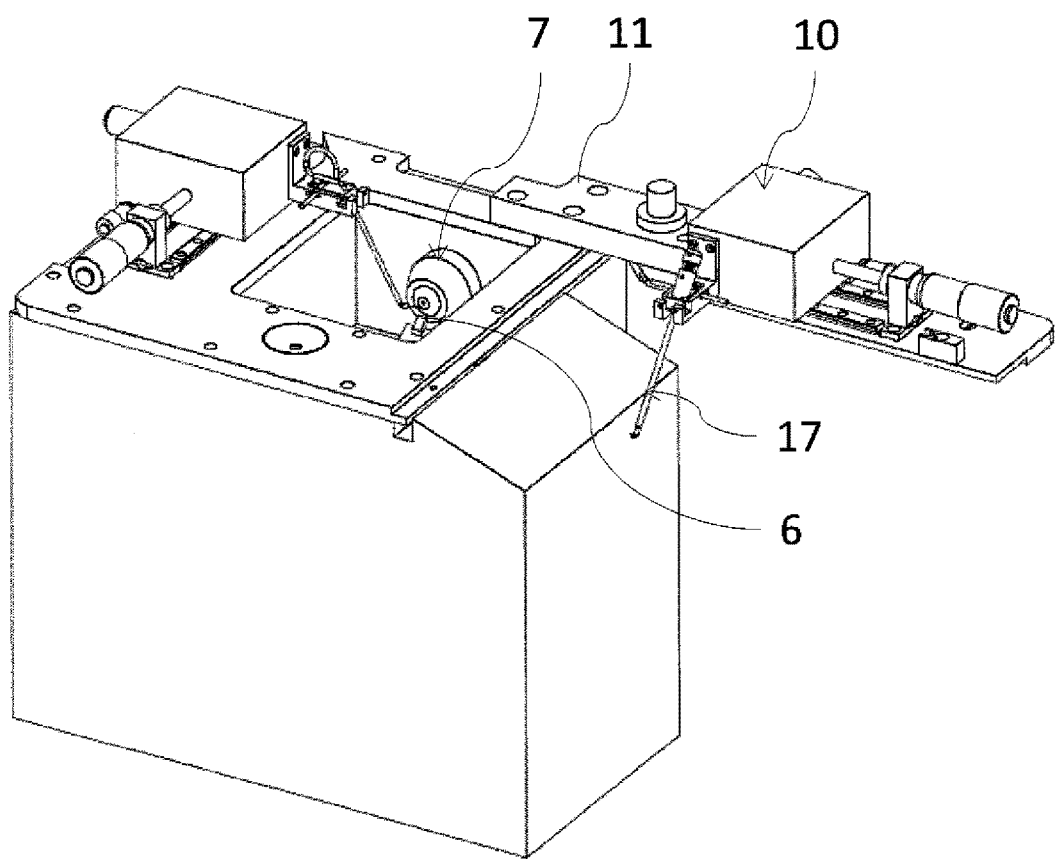
FIG. 2 shows an overall view of the device constructed on a schematically sketched, commercial cryostat without ionization device, wherein the second micromanipulator with the grid holder is arranged outside the working field by rotation about a vertical rotary axis.

A first micromanipulator 3 is attached exchangeably to the cover 2 of the boundary of a cryostat (cryostat 1) or an uncooled ultramicrotome apparatus, and has an apparatus for adjustment in the three spatial axes x, y, z (FIG. 1A). The cryostat 1 surrounds the working space for the cutting process in the microtome apparatus and allows access to the cutting process through an opening of the cover 2, preferably from above. This first micromanipulator 3 guides the section ribbon manipulator 4 according to the invention in the three spatial axes and brings its tip 5 into the desired positions. The section ribbons are formed on the edge of a diamond or glass knife 6 of an ultramicrotome with a microtome arm 7, shown here merely diagrammatically (FIG. 2). A ribbon of cryosections which are formed on the cut edge of this knife 6 by the advance and upward and downward movement of the microtome arm 7 is connected to the tip 5 by electrostatic attraction and can thus be easily manipulated.

Figure 1B:
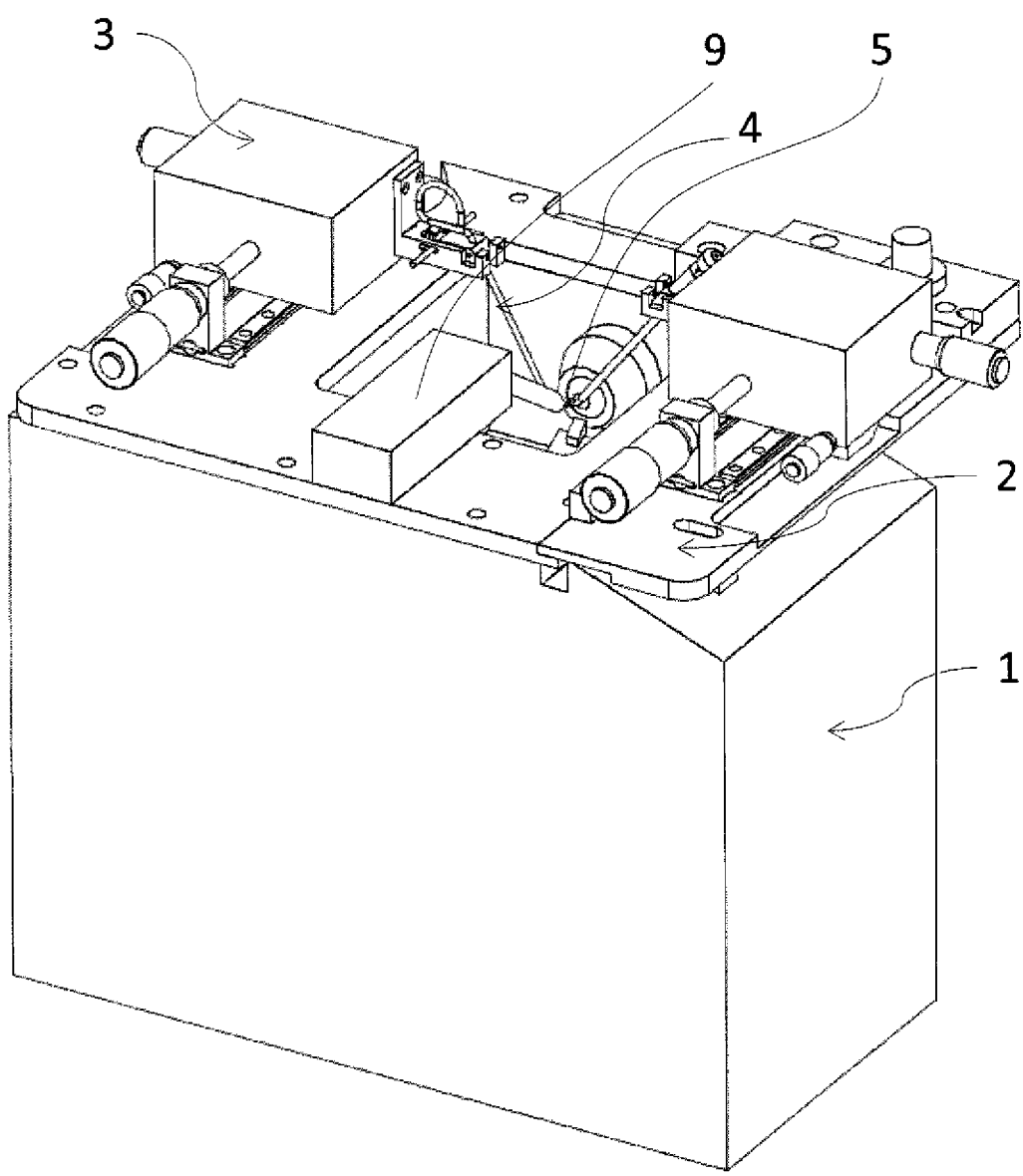
FIG. 1B is an overall view of the device with ionization device inserted.

The opening 8 in the cover 2 is a docking point made of magnetizable material for a commercially available ionization device 9 (FIG. 1B). This can be operated by foot pedals which are not shown in the figure. In discharge mode, the adhesion of the freshly formed sections to the knife surface is reduced. Charge mode is used for two purposes. Firstly, using this the short section ribbon which is initially formed is connected (tacked) to a conductive fiber, and secondly the long section ribbon which is formed as a result of the microtomisation is irreversibly attached to a correspondingly positioned grid (for example ionization device Leica EM FC 7 CRION: Charge Mode, Discharge Mode).

A second micromanipulator 10 is attached to an arm 11 of the cover 2 which can be rotated about a vertical axis (FIG. 2 and FIG. 10) and also has an apparatus for adjustment in the three spatial axes x, y, z. The second micromanipulator guides the electrically conductive grid for the TEM microscopy using a grid holder 17 and can be guided, independently of the first micromanipulator, autonomously in the three spatial directions. The second micromanipulator 10 which is attached to the arm 11 can in this way be moved, by rotation about a vertical axis, beyond the outline of the cover 2, offering the great advantage that when the arm 11 is in the "rotated out" state, the operator has free and unhindered access to the working space inside the cryostat and thus can observe without obstruction the progress of adhesion of the section ribbons to the section ribbon manipulator 4, and control this if necessary.

The entire manipulation of both the sections ribbons and the TEM grid takes place using these two micromanipulators by an operator from outside the working chamber for the cutting process in the microtome apparatus.

Figure 3A:
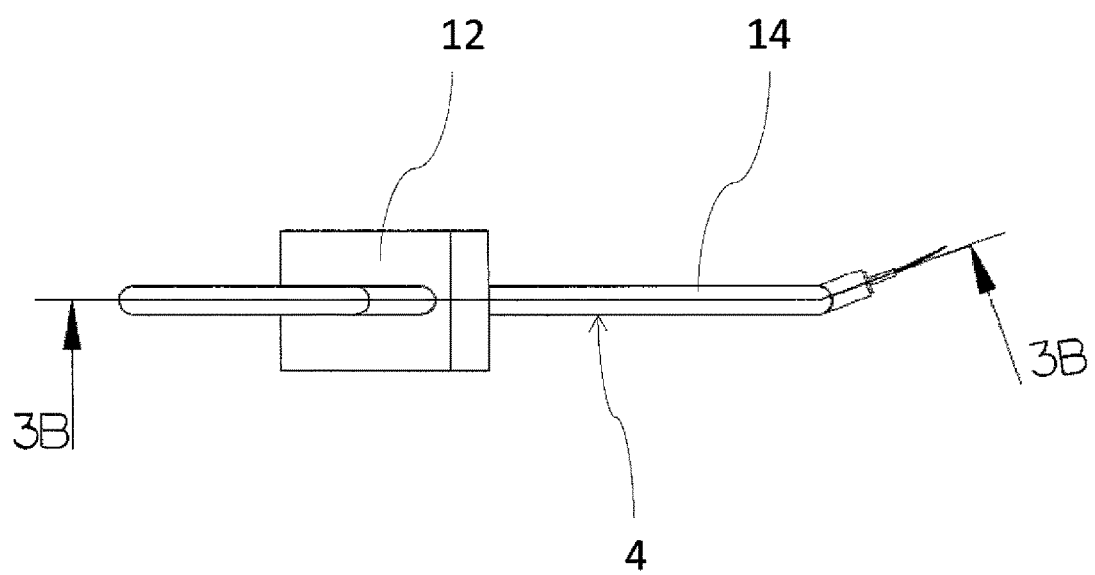
FIG. 3A is a top view of the section ribbon manipulator with the fiber tip.

The section ribbon manipulator 4 shown in FIGS. 3A and 3B is easily and quickly connected to the first micromanipulator 3 with a connecting piece 12 which is made of metal, and can easily and quickly be removed from this. A recess in the connecting piece 12 guides a thin metal tube 13, preferably of stainless steel, which is bent or angled at its end. The tube 13 is surrounded by an exchangeable electrically isolating plastic layer 14 which preferably consists of a shrink hose and is applied to the tube 13 by shrinkage.

Figure 3C:
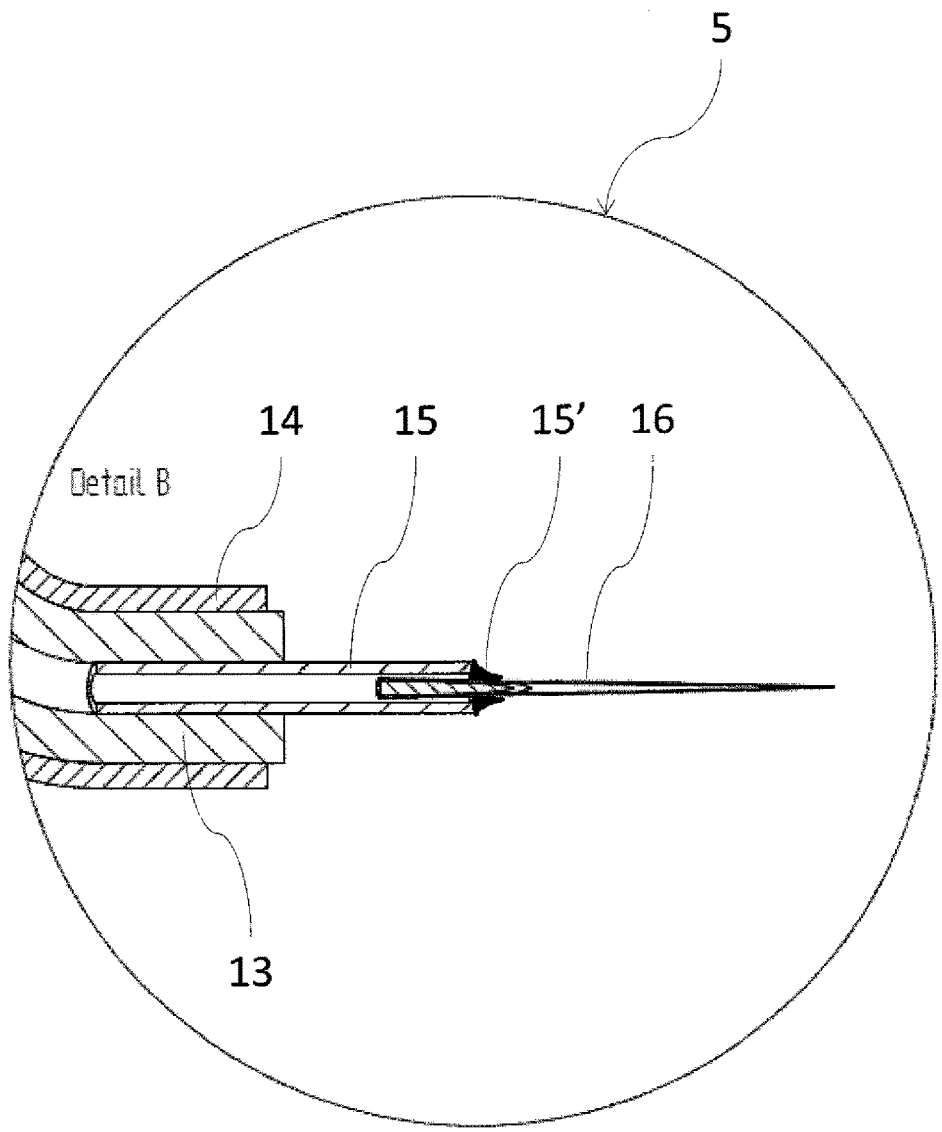
FIG. 3C shows an enlarged detail B of the tip of the section ribbon manipulator.

The assembled tip 5 is inserted in the angled part of the interior of the tube 13 (FIG. 3C). This tip 5 consists of a thin metal tube 15 in which a fiber 16 (for example an animal or human hair), a glass or plastic fiber, or a thin metal wire, is inserted and fixed exchangeably using an electrically conductive adhesive 15', for example with "liquid carbon", an adhesive with an added metal powder. The fiber 16 preferably has a maximum diameter of around 200 µm and preferably a length of a few millimeters. The assembled tip 5 can easily be exchanged in the interior of the tube 13 in that it is inserted into this interior using tweezers. The angled end of the tube 13, and the force used upon insertion, act to anchor (wedge) the tube 15 in position by form fit, in an exchangeable but nonetheless form-stable manner.

Before insertion, the surface of the fiber 16 is made electrically conductive by coating (for example by coating with a sputter source or vapour deposition under rotation in a vacuum) with an electrically conductive surface layer of a metal or carbon. The material of this surface layer is preferably selected from one or more of the following materials: gold, silver, copper, nickel, palladium, platinum, cobalt, but also carbon. This electrically conductive surface layer allows the tip 5 to be earthed during use of the method, where necessary for handling the section ribbons. Before coating, the fiber 16 is cleaned using solvent which is suitable for degreasing of hairs, preferably acetone, and then in the manner shown attached to the tube 15, for example with the conductive carbon already mentioned or another electrically conductive adhesive.

A plurality of tubes with the fibers 16 attached thereto are then coated together in the same work process. The layer thickness of the conductive surface layer, for metals, is preferably between 30 and 50 nm. The metal layers are sputtered onto the surface. This is achieved using a glow discharge with an argon gas pressure of preferably 0.1 mbar, by bombarding a target of the desired metal, which for example is produced in dish form. The metal clusters ejected from the target are distributed in the recipient, covering this and also the object to be coated according to the sputter energy applied and the duration of the coating process.

The carbon is vapour-deposited, preferably in a vacuum ($p<10^{-5}$ mbar) (so-called electron bombardment or resistance vapour deposition). Experiments have shown that the optimum layer thickness of the carbon is between 10 and 20 nm. Thicker layers can easily break and detach from the surface of the coated fiber 16.

The fibers 16 which are coated with metal or carbon in this way can be used repeatedly with careful handling. If the tip of the fiber is covered with section residue, it can be removed from the cryostat for short periods together with the section ribbon manipulator and thawed at room temperature. Conductive fibers are damaged under excessive deformation. This can occur if the fiber accidentally "rides over" the cutting edge of the knife, or the section ribbon manipulator is positioned unsuitably in the cryostat or removed carelessly after the end of work.

Figure 3D:
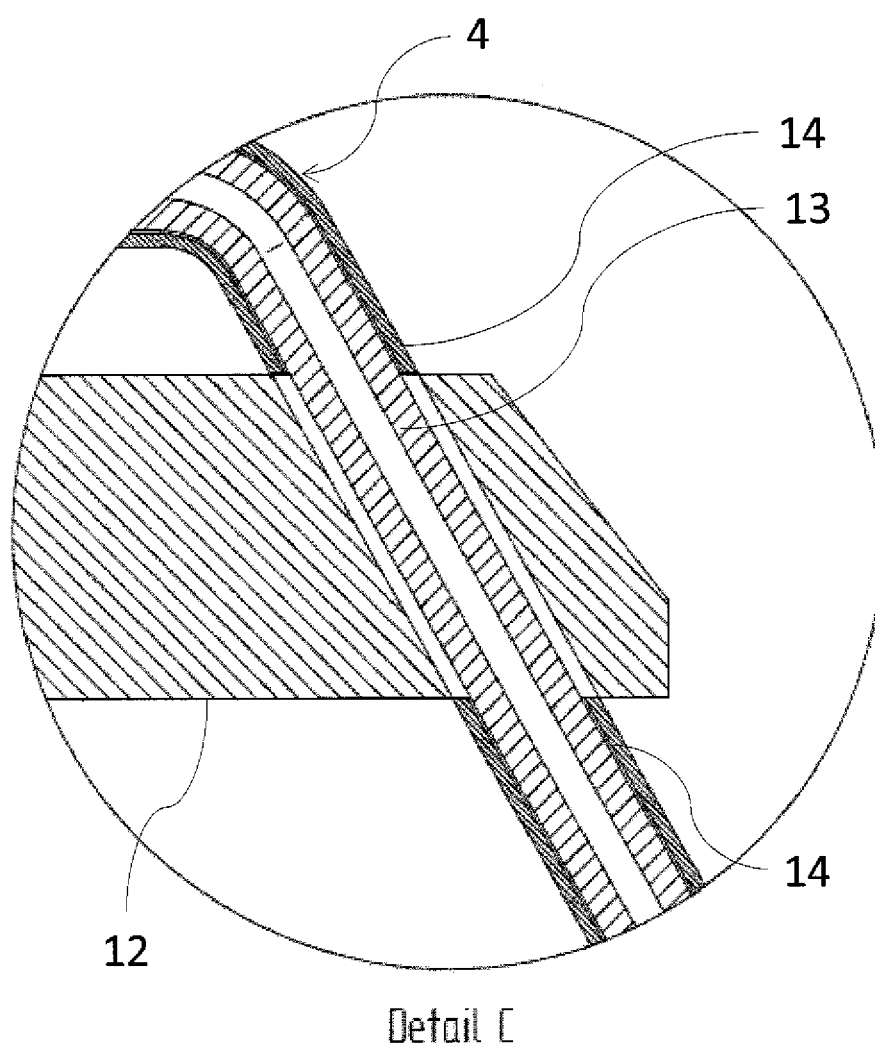
FIG. 3D shows an enlarged detail C of the connecting piece with inserted section ribbon manipulator.

The connecting piece 12 and metal tube 13 are connected together electrically conductively. As shown in FIG. 3D, to this end the carbon layer 14 around the tube 13 is interrupted at the connecting piece 12. This creates the electrical contact between the tube 13 and the connecting piece 12 and allows earthing of the tube 13 where suitable in the course of the process.

Figure 4A:
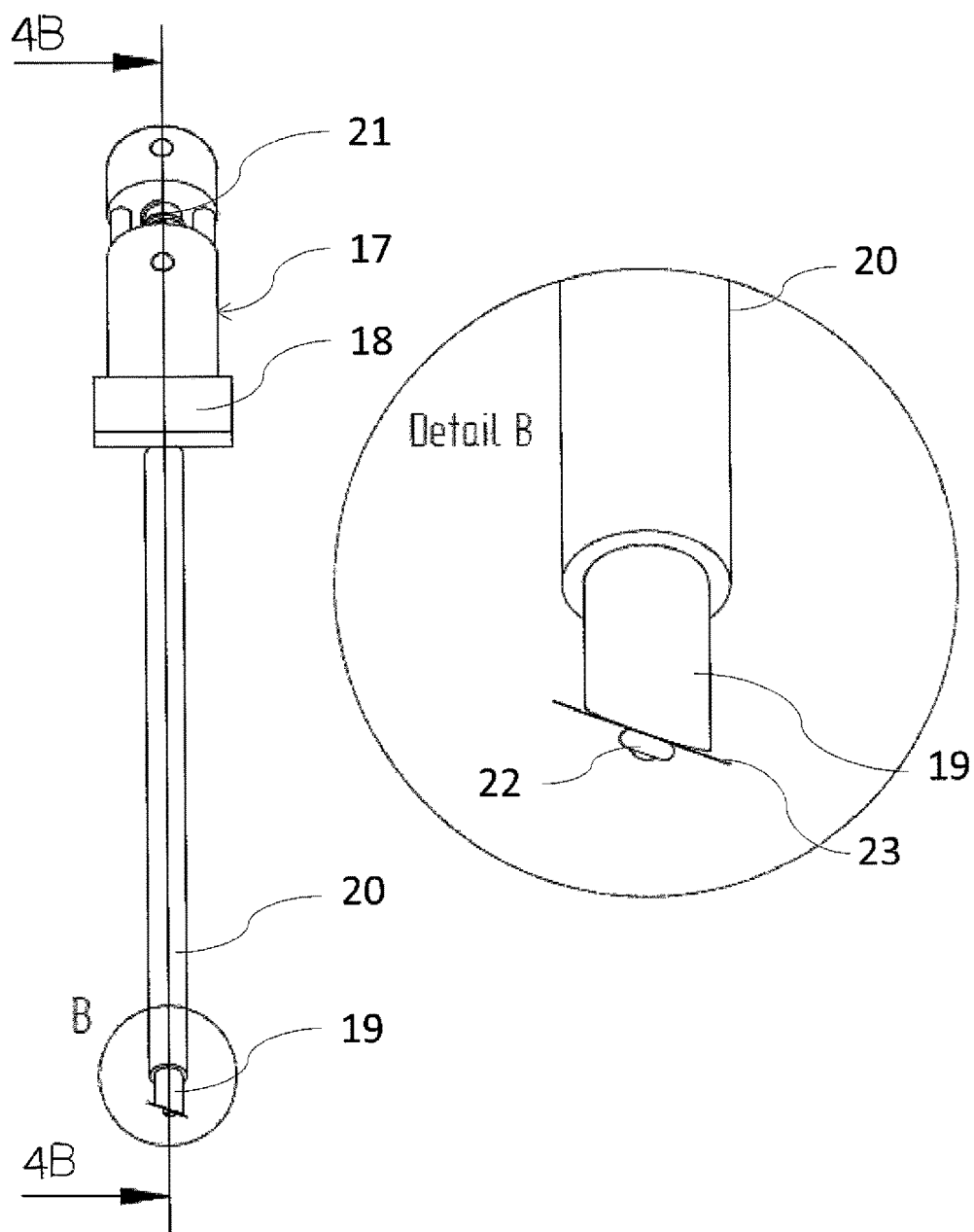
FIG. 4A is a top view of the grid holder with enlarged detail B.

As shown in FIGS. 4A and 4B, a grid holder 17 for a TEM grid 23 is installed exchangeably in the second micromanipulator 10. The metallic connecting piece 18 is punctured by a metal tube 19, preferably of stainless steel, which is connected electrically conductively to the connecting piece 18. The tube 19 has an electrically insulating plastic coating 20, preferably of a shrink hose. This terminates below the connecting piece 18, creating the electrical contact between the tube 19 and the connecting piece 18 and allowing earthing of the tube 19 where suitable in the course of the process.

Figure 4C:
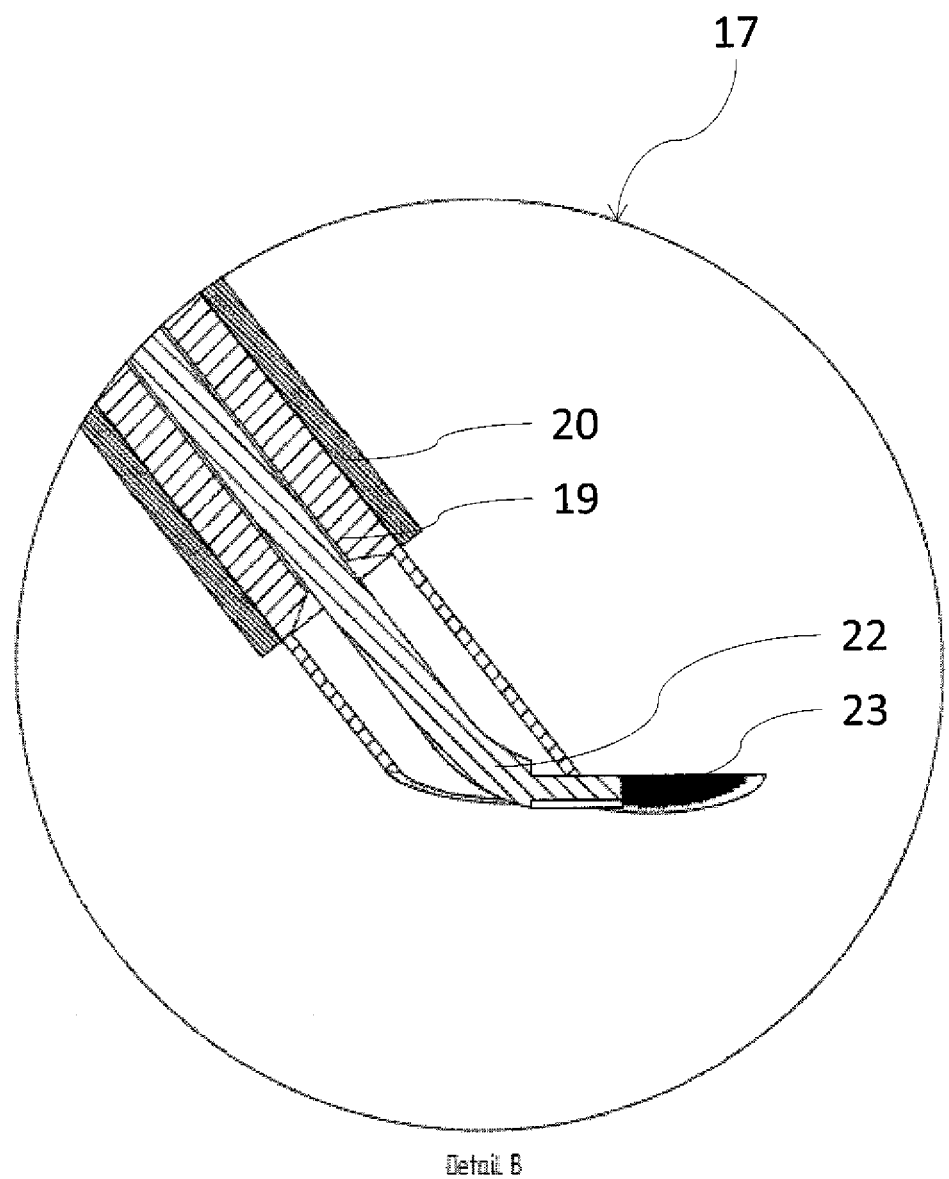
FIG. 4C shows an enlarged detail B of the tip of the grid holder with inserted grid.
Figure 4D:
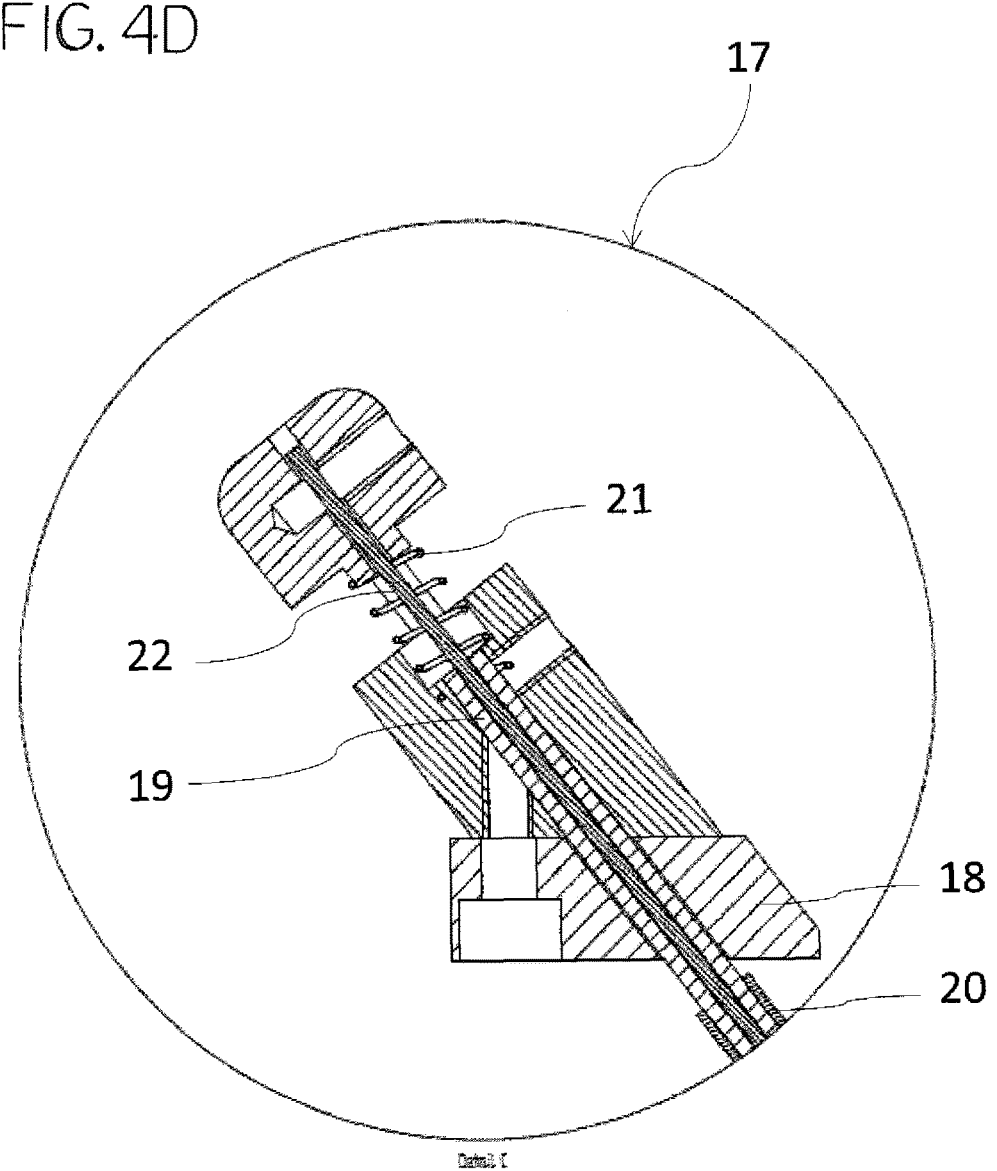
FIG. 4D shows an enlarged detail C of the connecting piece with inserted grid holder.

A spring mechanism 21 is provided at the upper end of the tube 19, which allows a thin wire or rod 22 to be pushed in the axial direction in the interior of the tube 19. Since this wire 22 is bent or angled at its end, as shown in enlarged detail in FIG. 4C, it is possible, by movement in the axial direction, to clamp a grid 23 (known in itself for use in TEM) exchangeably between the tube 19 and the wire 22 and release this again. Under the action of force on the spring mechanism 21 (shown in enlarged detail in FIG. 4D), the wire 22 is moved forward in the axial direction inside the tube 19 and hence a space is created for insertion of the grid 23 between the end of the tube 19 and the angled end of the wire 22. By relaxing (releasing) the spring mechanism, the end of the wire 22 is retracted in the axial direction and hence the grid 23 is exchangeably clamped at this place. Reactivation (compression) of the spring mechanism 21 releases the clamped grid 23 again.

As shown in enlarged detail B in FIG. 4A, the ends of the tube 19 and wire 22 are designed such that the clamped grid 23 does not lie horizontally but slightly obliquely to the section ribbon which is formed at the knife edge 6. This means that the edge of the grid 23 which is facing the cutting edge of the knife 6 lies higher than the edge of the grid facing away from the knife edge.

A grid 23, as used as a specimen carrier in transmission electron microscopy, is clamped in the grid holder 17 in this way. Such grids 23, which are known in themselves, have different mesh widths for use in TEM, the preferred diameter is 3 mm, the preferred layer thickness 30 µm. This grid 23 consists at least partly of an electrically conductive material such as copper, gold or molybdenum, which is usually coated with a thin (around 10 nm thick) electrically conductive layer, preferably a carbon layer. Preferably, commercially available grids, such as for example C-Flat™ (Electron Microscopy Sciences, Hatfield, Pa., US) are used. These are copper grids which are coated with a carbon layer around 10 nm thick, and suitably have defined holes (hole diameter for example between 1 and 2 µm) in a regular arrangement.

Figure 5A:
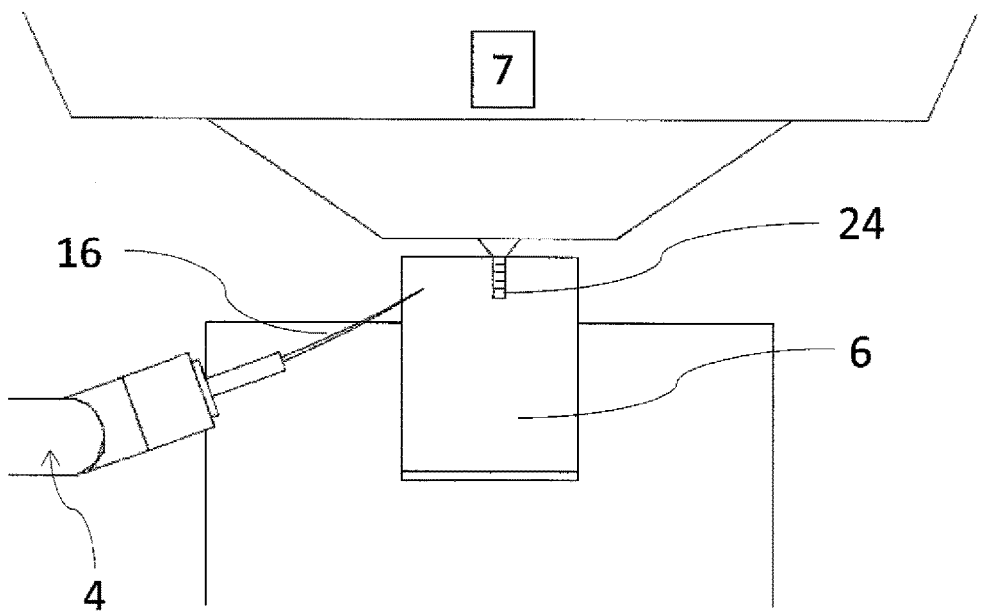
FIGS. 5A to 9B show the different phases I to VI of the method according to the invention for manipulation of section ribbons using the device according to the invention as an example. These show.

The method for use of the device according to the invention comprises six individual steps which are designated phases I to VI:

Phase I: In the starting position, the first sections are on the microtome knife 6 and the leading fiber tip 16 of the section ribbon manipulator 4 does not yet touch the still short section ribbon 24 (FIG. 5A).

Figure 5B:
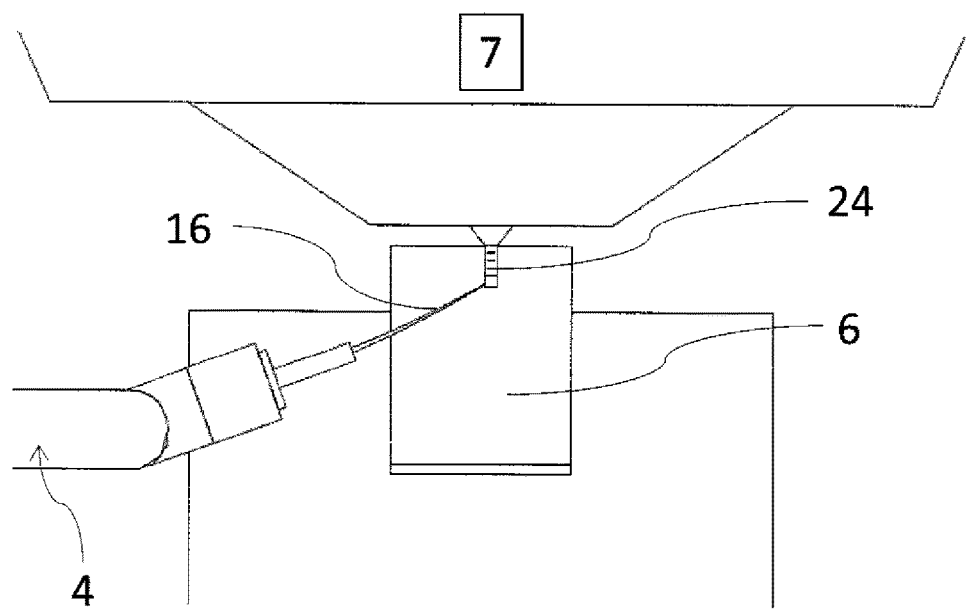
Figure 5C:
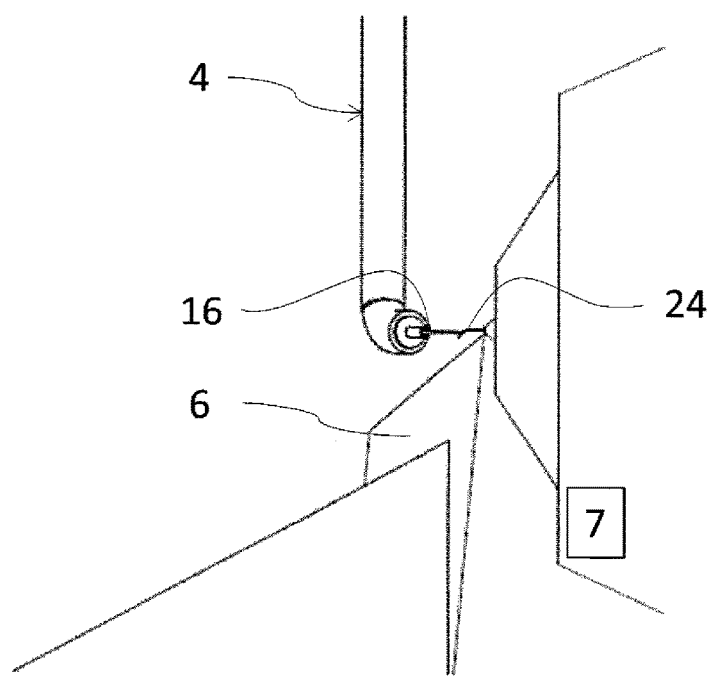

Phase II: The electrically conductive and earthed tip 16 is brought between the knife 6 and the first sections of the forming section ribbon 24. Using the first micromanipulator 3, it is brought from below into contact with the section ribbon 24 emerging from the microtome, and by a brief increase in ionization (charge mode) and the resulting electrostatic attraction, is firmly connected to the section ribbon 24 (FIGS. 5B and 5C). This offers the advantage that the tip 16 is reliably connected to the section ribbon 24, which is excluded with a non-electrically-conductive fiber.

Figure 6A:
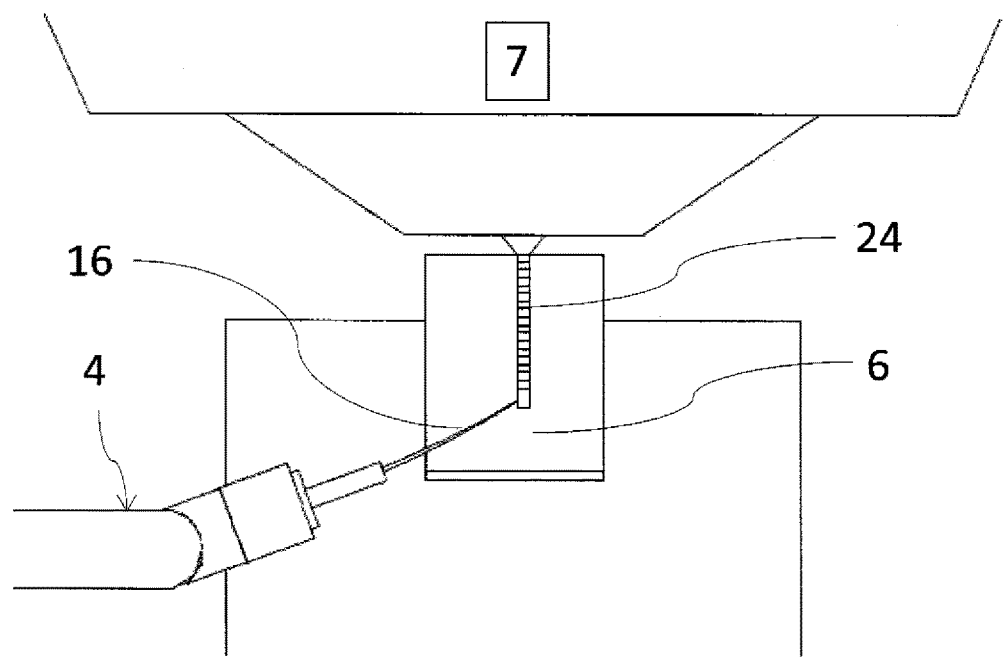
Figure 6B:
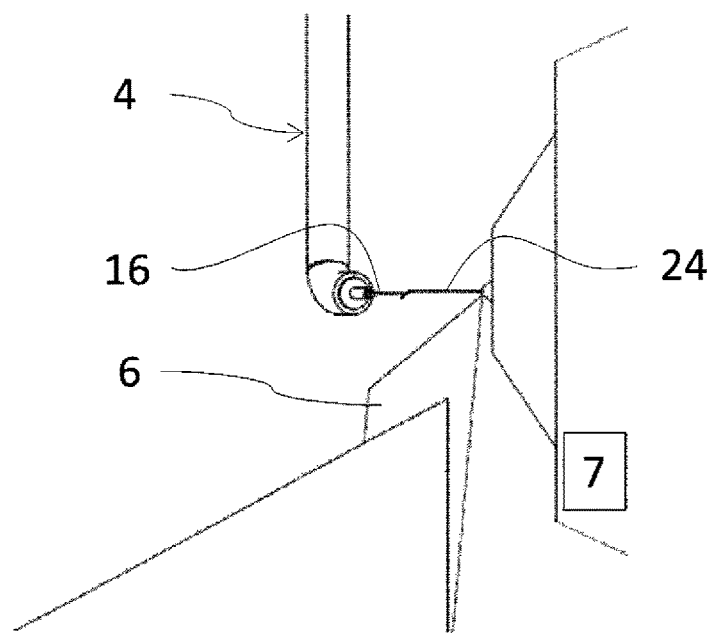

Phase III: After this fixing, the fiber tip 16 with the section ribbon adhering thereto is moved as far as possible away from the knife 6 of the microtome. By production of new sections of the specimen by microtomisation, the section ribbon 24 is extended and must be stretched horizontally by drawing back the fiber tip 16 of the section ribbon manipulator 4 using the micromanipulator 3. After emergence of the section ribbon from the microtome, only a minimum tension is exerted on the section ribbon which is usually mechanically very fragile, and by retracting the fiber tip 16 in the horizontal direction, the sag of the section ribbon following the microtome output is prevented. FIGS. 6A and 6B show as an example how the section ribbon 24 which is formed on the knife 6 in the cryostat with the microtome arm 7 is guided using the section ribbon manipulator 4. During the cutting process, the ionizer is in discharge mode with corresponding power. When the section ribbon 24 has been produced, the ionizer is switched off.

Figure 7A:
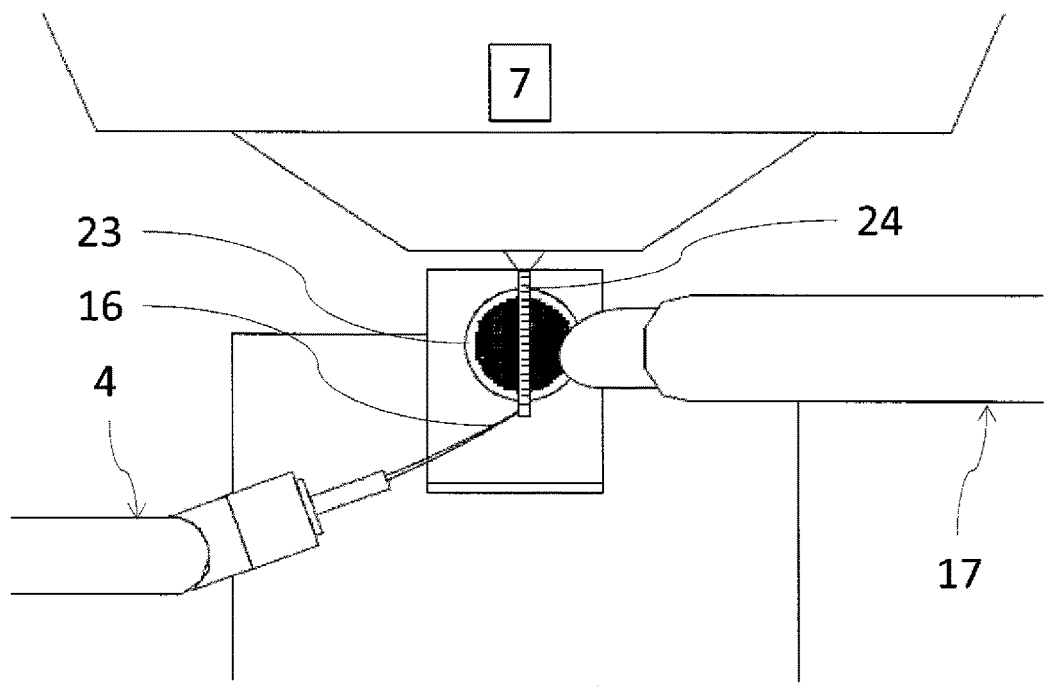

Phase IV: Positioning of the TEM grid, consisting of a metal film coated with a thin (approx. 10 nm thick) carbon layer, below the section ribbon. As shown in FIG. 7Aa, the grid 23 is positioned below the section ribbon 24, using the grid holder 17 which is guided by the second micromanipulator 10, when the section ribbon 24 cut from the specimen has reached the desired length. The application and correct positioning of the grid 23 on the grid holder 17 using the spring mechanism 21 are simple and efficient. Thus the grid 23 can quickly be exchanged and manipulated.

Figure 7B:
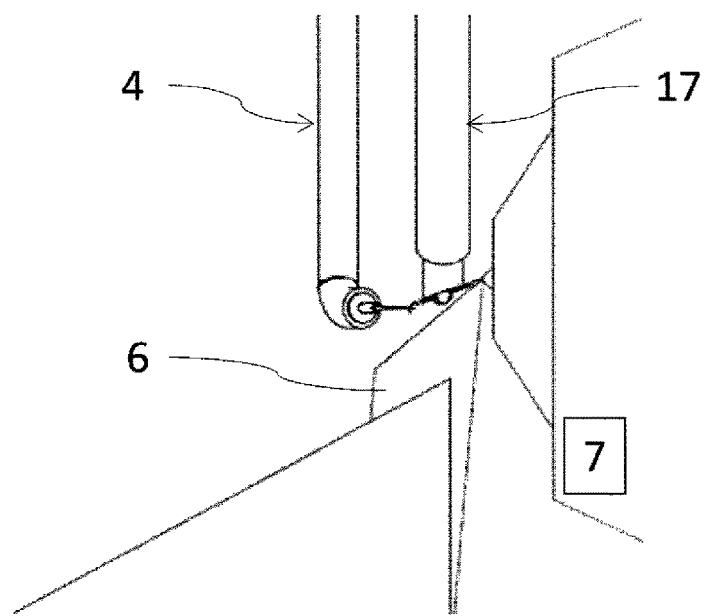

Phase V: Fixing of the section ribbon on the grid; separation from the fiber tip. When the section ribbon 24 has reached the desired length and the grid 23 is placed in the desired oblique position below the section ribbon 24 using the second micromanipulator 10, by moving the grid 23 in the vertical direction the section ribbon 24 is brought into contact with the grid 23 on the edge facing the knife, and at the same time the fiber tip 16 is lowered with the first micromanipulator 3 so that the section ribbon 24 comes to lie closely on the surface of the grid 23 (FIG. 7B). By an ionization pulse lasting a few milliseconds (charge mode), the two are then brought into contact with each other and the section ribbon 24 is thus irreversibly attached to the grid 23. This phase V is shown in overview in FIG. 10.

Figure 8A:
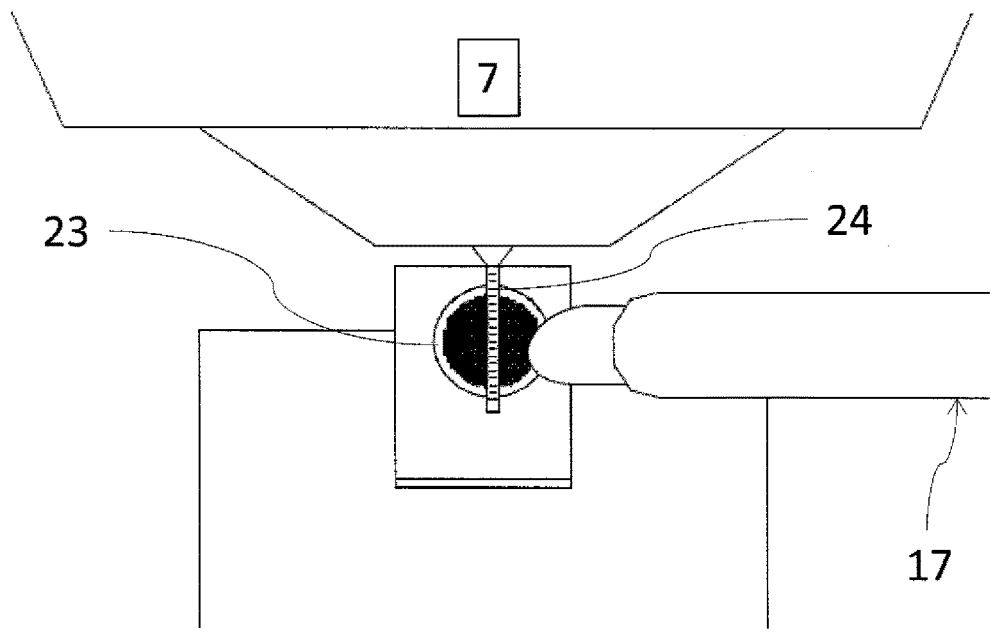
Figure 8B:
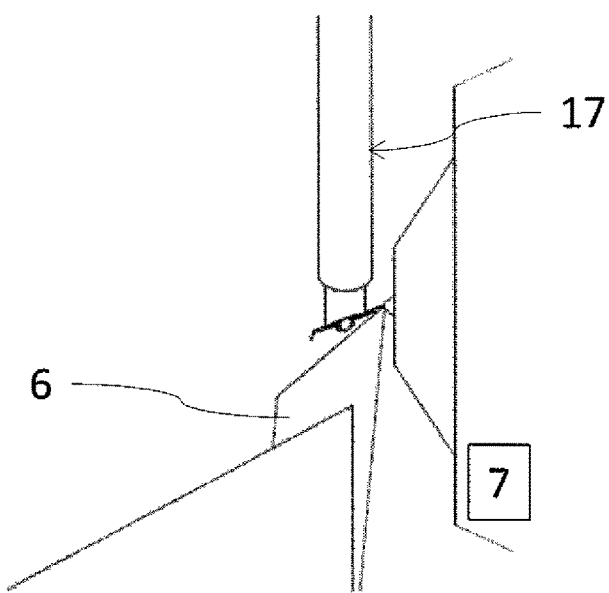

Phase VI: Cutting or tearing of the section ribbon on the grid, separation from the ultramicrotome: After fixing the section ribbon 24 on the grid 23 the fiber tip is moved away from the section ribbon 24 and hence the connection between the two is broken (FIGS. 8A and 8B).

Figure 9A:
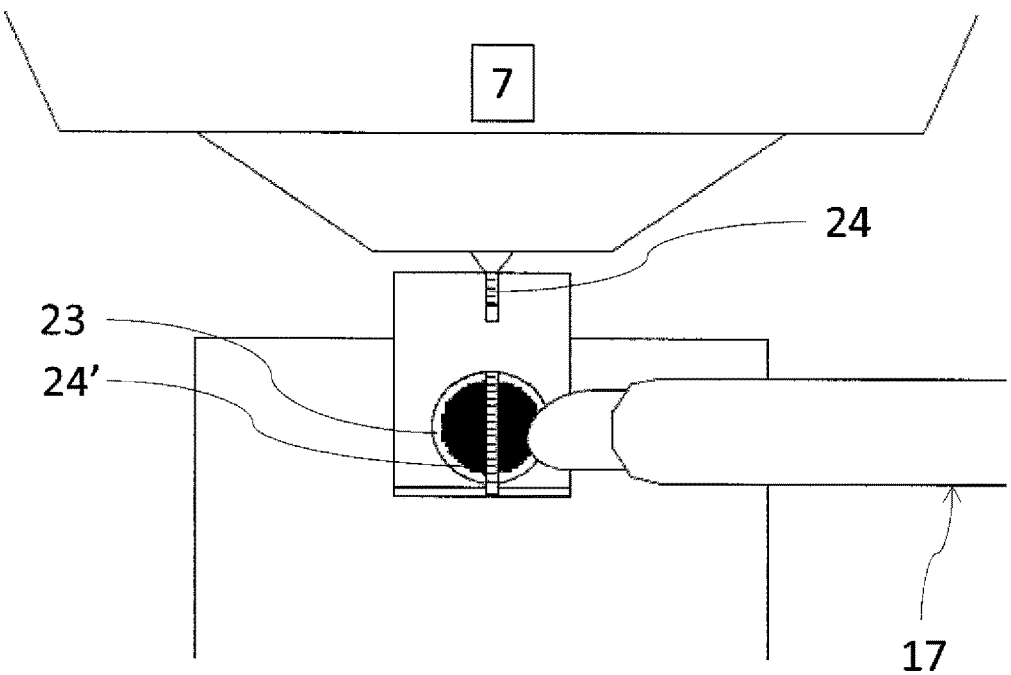
Figure 9B:
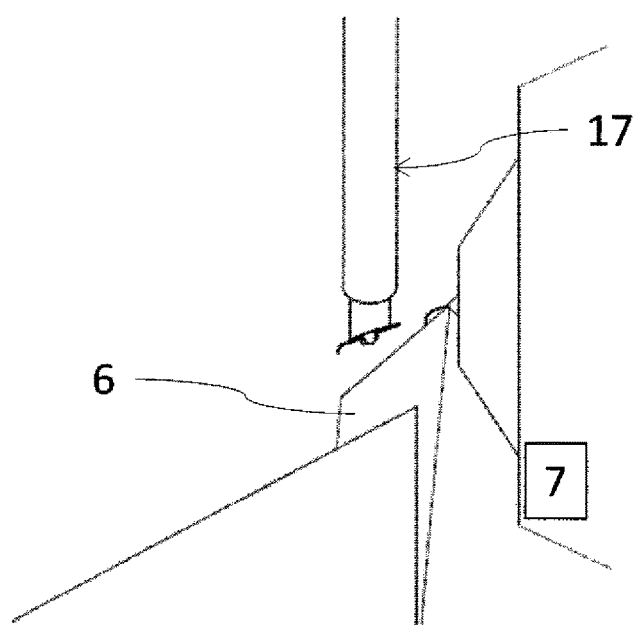

Finally, by suitable movement of the section ribbon 24 in its longitudinal axis, the part of the section ribbon 24' adhering to the grid 23 is separated from the rest. Now the part of the section ribbon 24' adhering to the grid 23 is removed from the device using the second grid holder 17 guided by the second micromanipulator 10 (FIGS. 9A and 9B). The section ribbon 24 attached to the grid is released from the grid holder 17 by simply pressing on the spring mechanism 21, and moved as quickly as possible into a commercially available transfer vessel filled with liquid nitrogen. In this form, the section ribbon 24 can be sent for examination, in particular in the TEM. Due to the short transfer time, the contamination with ice crystals is reduced in comparison with the known method.

The advantage of this method is that no highly developed fine motor skills are required by the operator in order to produce cryosections successfully, since all demanding steps are carried out by micromanipulators which are easy to operate. These are designed so that the function of the magnifying glass, mounted swivelably above the cryostat for observation in commercial microtomes, is not obstructed (over-large manipulators prevent the unhindered swiveling of the magnifying glass). Furthermore, the rotatability of the grid micromanipulator, shown in FIG. 2 and FIG. 10, about a vertical rotary axis on the arm 11 is of great benefit, since using this a fiber which is guided by hand on an isolated rod (preferably wood) can be brought into the cryostat in order e.g. to free the knife from undesirable sections and possible ice contamination.

An important advantage of the invention is the rapid manipulation of the grid 23 in the case of cryosectioning after successful fixing of the sections on the grid 23. Ice crystals are always present in the cryostat. If these adsorb on the sections in the cold nitrogen gas atmosphere, the structures below are no longer suitable for examination in the TEM since electrons cannot propagate through small ice crystals (diameter<0.5 microns) irradiated in the electron microscope. Under liquid nitrogen however no ice crystals adsorb onto the sections. Rapid transfer of the section ribbons 24 adsorbed on the grid 23, as enabled by the device according to the invention, is therefore of great preparative benefit.

The method for transfer of the section ribbons emerging from the microtome to a TEM carrier can be used both for specimens of biological origin (tissue specimens) and for specimens of other materials (for example high-polymer plastics). It is equally suitable for working at room temperature and at temperatures in the cryoregion between 190° K. and 110° K., preferably around 120° K.

The invention claimed is:

1. Device for transferring a section ribbon to a specimen holder for use in transmission electron microscopy (TEM), the section ribbon being transferred to the specimen holder by way of an ionization device in a microtome apparatus, wherein the device has two mutually independent tools comprising a first tool and a second tool, the first tool having a metal tube for manipulating the section ribbon and the second tool being adapted to manipulate the specimen holder, each of the first tool and the second tool being positionable independently by way of two mutually independent micromanipulators, wherein the first tool has a tube of an electrically insulating material and an exchangeable tip, the tip comprising a thin metal tube and a resilient fiber of dielectric material having an electrically conductive surface coating, the fiber being exchangeably connected to an end of the thin metal tube by an electrically conductive adhesive.

2. Device according to claim 1, wherein the electrically insulating material is interrupted in the region of a connecting piece so that an electrically conductive connection can be created between the metal tube and the connecting piece.

3. Device according to claim 1 wherein the first tool is angled at an end.

4. Device according to claim 3 wherein the end of the first tool is angled by around 45° to its longitudinal axis.

5. Device according to claim 1, wherein the resilient fiber is a hair of human or animal origin.

6. Device according to claim 1, wherein the resilient fiber has a maximum diameter of around 200 µm and a length of a few millimeters.

7. Device according to claim 1, wherein the electrically conductive surface coating consists of at least one metal.

8. Device according to claim 7 wherein the electrically conductive surface coating consists of at least one of the following metallic materials: gold, silver, copper, nickel, palladium, platinum, and cobalt.

9. Device according to claim 1, wherein the electrically conductive surface coating has a layer thickness of 30 to 50 nm.

10. Device according to claim 1, wherein the resilient fiber has a surface coating of carbon.

11. Device according to claim 10 wherein the surface coating of carbon has a layer thickness of 10 to 20 nm.

12. Device according to claim 1, wherein the microtome apparatus includes a cryostat having a cover, and wherein the micromanipulator of the second tool is arranged to be rotatable about a vertical axis on an arm which is mounted on the cover of the cryostat.

13. Device according to claim 1, wherein the second tool comprises a metal tube, an electrically insulating coating, a wire inside the metal tube and a spring mechanism with which the wire can be moved within the metal tube in the axial direction.

14. Device according to claim 13 wherein the metal tube is of stainless steel and the electrically insulating coating is a shrink hose.

15. Device according to claim 13, wherein the electrically insulating coating surrounds the metal tube and is interrupted in the region of a connecting piece, so that an electrically conductive connection can be created between the metal tube and the connecting piece.

16. Device according to claim 13, wherein the wire is angled at one end.

17. Device according to claim 16 wherein the end of the wire is angled by around 45° to its longitudinal axis.

18. Device according to claim 16, wherein the second tool is adapted to allow the gripping and releasing of a specimen holder by way of activation of the spring mechanism to move the bent end of the wire relative to the end of the metal tube.

19. Device according to claim 13, wherein the microtome apparatus has a knife for cutting the section ribbons, and wherein the end of the metal tube and the wire are formed so that in use the specimen holder is positioned not horizontally but obliquely relative to the section ribbon to be transferred, the edge of the specimen holder facing the knife being higher than the edge of the specimen holder facing away from the knife.

* * * * *